United States Patent
Bartol et al.

(10) Patent No.: US 9,039,630 B2
(45) Date of Patent: May 26, 2015

(54) METHOD OF DETECTING A SACRAL NERVE

(75) Inventors: Stephen Bartol, Windsor (CA); Christopher Wybo, Royal Oak, MI (US)

(73) Assignee: Innovative Surgical Solutions, LLC, Wixon, MI (US)

(*) Notice: Subject to any disclaimer, the term of this patent is extended or adjusted under 35 U.S.C. 154(b) by 286 days.

(21) Appl. No.: 13/591,273

(22) Filed: Aug. 22, 2012

(65) Prior Publication Data

US 2014/0058283 A1 Feb. 27, 2014

(51) Int. Cl.
*A61B 5/11* (2006.01)
*A61B 5/20* (2006.01)
*A61B 5/00* (2006.01)

(52) U.S. Cl.
CPC ............. *A61B 5/1104* (2013.01); *A61B 5/1107* (2013.01); *A61B 5/205* (2013.01); *A61B 5/4047* (2013.01); *A61B 5/4052* (2013.01)

(58) Field of Classification Search
CPC .. A61B 5/1104; A61B 5/1107; A61B 5/4052; A61B 5/4047; A61B 5/205
USPC .......................... 600/554, 587, 591, 593, 595
See application file for complete search history.

(56) References Cited

U.S. PATENT DOCUMENTS

| | | |
|---|---|---|
| 3,200,814 A | 8/1965 | Taylor et al. |
| 3,565,080 A | 2/1971 | Ide et al. |
| 3,797,010 A | 3/1974 | Adler et al. |
| 4,817,628 A | 4/1989 | Zealear et al. |
| 4,887,610 A * | 12/1989 | Mittal ........................... 600/546 |
| 5,284,153 A | 2/1994 | Raymond et al. |
| 5,284,154 A | 2/1994 | Raymond et al. |
| 5,533,515 A * | 7/1996 | Coller et al. ................... 600/593 |
| 5,775,331 A * | 7/1998 | Raymond et al. ............. 600/554 |
| 6,086,549 A * | 7/2000 | Neese et al. ................... 600/587 |
| 6,324,432 B1 | 11/2001 | Rigaux et al. |
| 6,361,508 B1 | 3/2002 | Johnson et al. |
| 6,466,817 B1 | 10/2002 | Kaula et al. |
| 6,500,128 B2 | 12/2002 | Marino |
| 6,564,078 B1 | 5/2003 | Marino et al. |
| 6,760,616 B2 | 7/2004 | Hoey et al. |

(Continued)

FOREIGN PATENT DOCUMENTS

| | | |
|---|---|---|
| EP | 1575010 A1 | 9/2005 |
| FR | 2920087 A1 | 2/2009 |

(Continued)

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

(Continued)

*Primary Examiner* — Sean Dougherty
*Assistant Examiner* — Michael C Stout
(74) *Attorney, Agent, or Firm* — Quinn Law Group, PLLC.

(57) ABSTRACT

A method of detecting the presence of a sacral nerve in a human subject includes providing an electrical stimulus within an intracorporeal treatment area of the human subject; detecting a physical response of at least one of an external sphincter of the bladder and an external sphincter of the anus; and providing an indication to a user if the detected physical response corresponds to the provided electrical stimulus.

21 Claims, 7 Drawing Sheets

(56) References Cited

U.S. PATENT DOCUMENTS

| | | | |
|---|---|---|---|
| 6,807,438 B1 | 10/2004 | Brun Del Re et al. | |
| 6,972,199 B2 | 12/2005 | Lebouitz et al. | |
| 7,050,848 B2 | 5/2006 | Hoey et al. | |
| 7,079,883 B2 | 7/2006 | Marino et al. | |
| 7,177,677 B2 | 2/2007 | Kaula et al. | |
| 7,207,949 B2 | 4/2007 | Miles et al. | |
| 7,216,001 B2 | 5/2007 | Hacker et al. | |
| 7,236,832 B2 | 6/2007 | Hemmerling et al. | |
| 7,470,236 B1 | 12/2008 | Kelleher et al. | |
| 7,522,953 B2 | 4/2009 | Kaula et al. | |
| 7,578,819 B2 | 8/2009 | Bleich et al. | |
| 7,582,058 B1 | 9/2009 | Miles et al. | |
| 7,657,308 B2 | 2/2010 | Miles et al. | |
| 7,664,544 B2 | 2/2010 | Miles et al. | |
| 7,668,588 B2 | 2/2010 | Kovacs | |
| 7,691,057 B2 | 4/2010 | Miles et al. | |
| 7,892,173 B2 | 2/2011 | Miles et al. | |
| 7,905,840 B2 | 3/2011 | Pimenta et al. | |
| 7,942,826 B1 | 5/2011 | Scholl et al. | |
| 7,959,577 B2 | 6/2011 | Schmitz et al. | |
| 7,962,191 B2 | 6/2011 | Marino et al. | |
| 7,981,058 B2 | 7/2011 | Akay | |
| 7,991,463 B2 | 8/2011 | Kelleher et al. | |
| 8,000,782 B2 | 8/2011 | Gharib et al. | |
| 8,016,776 B2 | 9/2011 | Bourget et al. | |
| 8,027,716 B2 | 9/2011 | Gharib et al. | |
| 8,055,349 B2 | 11/2011 | Gharib et al. | |
| 8,068,912 B2 | 11/2011 | Kaula et al. | |
| 8,075,499 B2 | 12/2011 | Nathan et al. | |
| 8,090,436 B2 | 1/2012 | Hoey et al. | |
| 8,133,173 B2 | 3/2012 | Miles et al. | |
| 8,137,284 B2 | 3/2012 | Miles et al. | |
| 8,147,421 B2 | 4/2012 | Farquhar et al. | |
| 8,147,429 B2* | 4/2012 | Mittal et al. | 600/591 |
| 8,165,653 B2 | 4/2012 | Marino et al. | |
| 8,343,065 B2 | 1/2013 | Bartol et al. | |
| 8,343,079 B2 | 1/2013 | Bartol et al. | |
| 2001/0031916 A1 | 10/2001 | Bennett et al. | |
| 2002/0038092 A1 | 3/2002 | Stanaland et al. | |
| 2002/0165590 A1 | 11/2002 | Crowe et al. | |
| 2003/0074037 A1 | 4/2003 | Moore et al. | |
| 2004/0068203 A1* | 4/2004 | Gellman et al. | 600/587 |
| 2004/0077969 A1 | 4/2004 | Onda et al. | |
| 2004/0122341 A1* | 6/2004 | Walsh et al. | 600/591 |
| 2004/0186535 A1 | 9/2004 | Knowlton | |
| 2004/0230138 A1 | 11/2004 | Inoue et al. | |
| 2004/0243018 A1 | 12/2004 | Organ et al. | |
| 2005/0027313 A1* | 2/2005 | Shaker | 606/197 |
| 2005/0075578 A1 | 4/2005 | Gharib et al. | |
| 2005/0085741 A1 | 4/2005 | Hoskonen et al. | |
| 2005/0102007 A1 | 5/2005 | Ayal et al. | |
| 2005/0240086 A1 | 10/2005 | Akay | |
| 2005/0245839 A1 | 11/2005 | Stivoric et al. | |
| 2005/0280531 A1 | 12/2005 | Fadem et al. | |
| 2005/0283204 A1 | 12/2005 | Buhlmann et al. | |
| 2006/0004304 A1* | 1/2006 | Parks | 600/593 |
| 2006/0020177 A1 | 1/2006 | Seo et al. | |
| 2006/0052726 A1 | 3/2006 | Weisz et al. | |
| 2006/0135888 A1 | 6/2006 | Mimnagh-Kelleher et al. | |
| 2006/0148735 A1* | 7/2006 | Rosenzweig et al. | 514/44 |
| 2006/0270949 A1 | 11/2006 | Mathie et al. | |
| 2007/0038155 A1 | 2/2007 | Kelly, Jr. et al. | |
| 2007/0265675 A1 | 11/2007 | Lund et al. | |
| 2007/0276270 A1 | 11/2007 | Tran | |
| 2007/0293792 A1* | 12/2007 | Sliwa et al. | 600/587 |
| 2008/0051643 A1 | 2/2008 | Park et al. | |
| 2008/0058656 A1 | 3/2008 | Costello et al. | |
| 2008/0161730 A1* | 7/2008 | McMahon et al. | 600/593 |
| 2008/0167695 A1 | 7/2008 | Tehrani et al. | |
| 2008/0234767 A1 | 9/2008 | Salmon et al. | |
| 2008/0287761 A1 | 11/2008 | Hayter et al. | |
| 2008/0306363 A1 | 12/2008 | Chaiken et al. | |
| 2008/0306397 A1 | 12/2008 | Bonmassar et al. | |
| 2008/0312560 A1 | 12/2008 | Jamsen et al. | |
| 2008/0312709 A1 | 12/2008 | Volpe et al. | |
| 2009/0024001 A1* | 1/2009 | Parks et al. | 600/300 |
| 2009/0036747 A1 | 2/2009 | Hayter et al. | |
| 2009/0062696 A1 | 3/2009 | Nathan et al. | |
| 2009/0069709 A1 | 3/2009 | Schmitz et al. | |
| 2009/0069722 A1 | 3/2009 | Flaction et al. | |
| 2009/0076336 A1 | 3/2009 | Mazar et al. | |
| 2009/0171381 A1 | 7/2009 | Schmitz et al. | |
| 2009/0192416 A1 | 7/2009 | Ernst et al. | |
| 2009/0228068 A1 | 9/2009 | Buhlmann et al. | |
| 2009/0247910 A1 | 10/2009 | Klapper | |
| 2009/0306741 A1 | 12/2009 | Hogle et al. | |
| 2009/0318779 A1 | 12/2009 | Tran | |
| 2010/0010367 A1* | 1/2010 | Foley et al. | 600/546 |
| 2010/0076254 A1* | 3/2010 | Jimenez et al. | 600/30 |
| 2010/0094143 A1* | 4/2010 | Mahapatra et al. | 600/486 |
| 2010/0137748 A1 | 6/2010 | Sone et al. | |
| 2010/0152619 A1 | 6/2010 | Kalpaxis et al. | |
| 2010/0152622 A1* | 6/2010 | Teulings | 600/595 |
| 2010/0152623 A1 | 6/2010 | Williams | |
| 2010/0168559 A1 | 7/2010 | Tegg et al. | |
| 2010/0228192 A1* | 9/2010 | O'Dea et al. | 604/104 |
| 2010/0292617 A1 | 11/2010 | Lei et al. | |
| 2010/0305479 A1* | 12/2010 | O'Dea | 600/587 |
| 2011/0004207 A1 | 1/2011 | Wallace et al. | |
| 2011/0028943 A1* | 2/2011 | Lawson et al. | 604/544 |
| 2011/0230782 A1* | 9/2011 | Bartol et al. | 600/546 |
| 2011/0230783 A1* | 9/2011 | Bartol et al. | 600/546 |
| 2011/0237974 A1 | 9/2011 | Bartol et al. | |
| 2012/0053491 A1 | 3/2012 | Nathan et al. | |
| 2012/0179063 A1* | 7/2012 | Bharucha et al. | 600/561 |
| 2013/0213659 A1 | 5/2013 | Bartol et al. | |
| 2013/0184612 A1* | 7/2013 | Quackenbush et al. | 600/587 |
| 2013/0281885 A1* | 10/2013 | Rowbottom et al. | 600/587 |

FOREIGN PATENT DOCUMENTS

| | | |
|---|---|---|
| WO | 0078209 A2 | 12/2000 |
| WO | 2007024147 A1 | 3/2007 |

OTHER PUBLICATIONS

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Pliers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

* cited by examiner

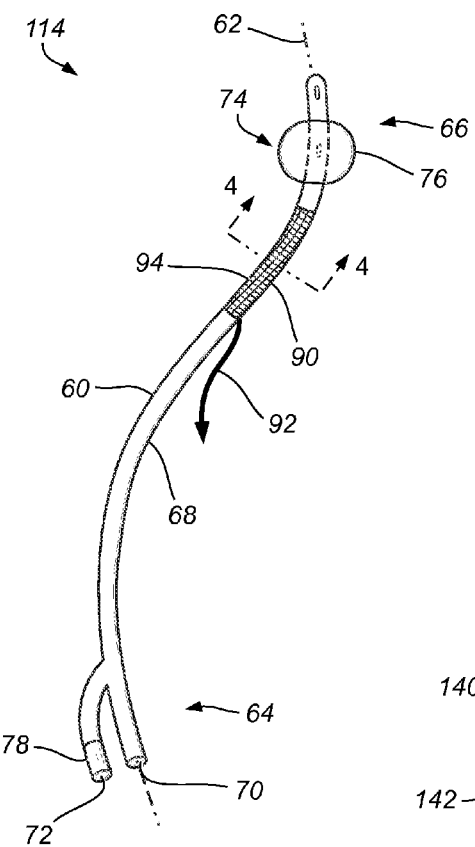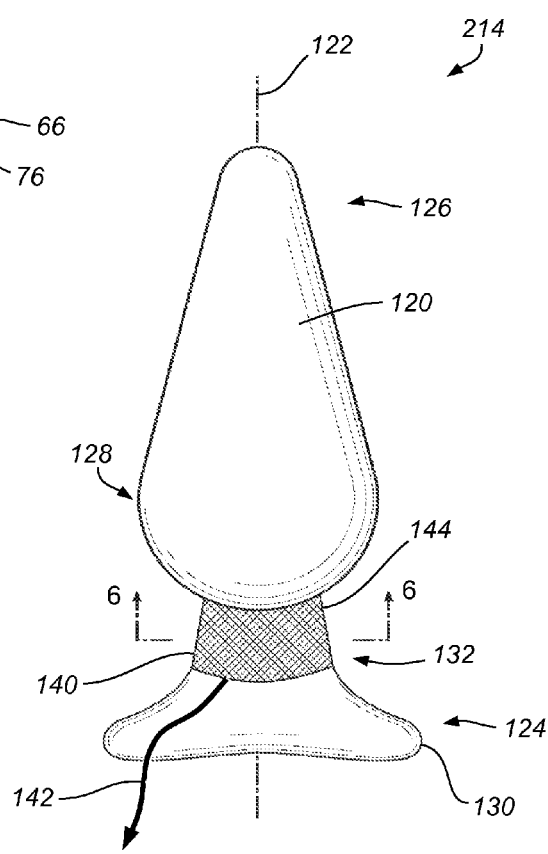
*FIG. 3*
*FIG. 5*
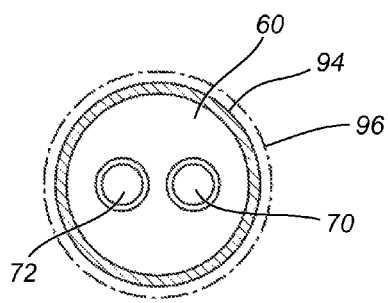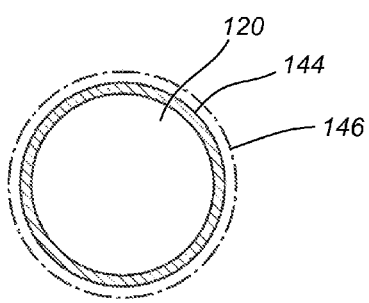
*FIG. 4*
*FIG. 6*

METHOD OF DETECTING A SACRAL NERVE

CROSS REFERENCE TO RELATED APPLICATIONS

This application is related to U.S. Patent Publication No. 2014/0058284, filed on the same date as this application and entitled "Nerve Monitoring System," and is related to U.S. Patent Publication No. 2014/0058288, filed on the same date as this application and entitled "Sphincter Contraction Sensor," which are hereby incorporated by reference in their entirety.

TECHNICAL FIELD

The present invention relates generally to a method of identifying the presence of the sacral nerve within a human subject.

BACKGROUND

The pudendal nerve and/or other sacral nerves originating from the sacral plexus include sensory and somatic nerves that innervate the external genitalia of both sexes. Additionally, these nerves innervate and control the contractions of the external sphincter of the anus and external sphincter of the bladder. A sphincter is an anatomical structure comprised mainly of circular muscle, which maintains constriction of a natural body passage or orifice and which relaxes as required by normal physiological functioning.

In humans, the pudendal nerve and/or other sacral nerves of particular concern are comprised of fibers exiting from the second, third, and fourth sacral vertebrae (i.e., S2-S4). During a pelvic floor surgery, for example, these nerves are at a significant risk of being stretched, pinched, torn, or otherwise injured. Any such damage may result in a temporary or permanent loss of nerve signal transmission, and may potentially cause urinary and/or fecal incontinence.

SUMMARY

A method of detecting the presence of a sacral nerve in a human subject includes: providing an electrical stimulus within an intracorporeal treatment area of the human subject; detecting a physical response of at least one of an external sphincter of the bladder and an external sphincter of the anus; and providing an indication to a user if the detected physical response corresponds to the provided electrical stimulus.

The step of providing an electrical stimulus may likewise include selectively administering the electrical stimulus from a distal end portion of an elongate probe. In this manner, the provided indication may correspondingly include an indication of proximity between the distal end portion of the elongate stimulator and the sacral nerve of the subject.

The step of detecting a physical response of at least one of the external sphincter of the bladder and the external sphincter of the anus may include: generating a mechanomyography output signal in response to a contact force of the at least one external sphincter of the bladder and the external sphincter of the anus against an elongate sphincter contraction sensor disposed within the at least one external sphincter of the bladder and the external sphincter of the anus.

The method may further include: calculating a change in the magnitude of the contact force from the mechanomyography output signal; comparing the change in the magnitude of the contact force to a threshold; and detecting a sphincter contraction if the change in the magnitude of the contact force exceeds the threshold.

Similarly, the method may include: computing a time derivative of the contact force from the mechanomyography output signal; comparing the time derivative of the contact force to a threshold; and determining that the mechanomyography output signal corresponds to the provided electrical stimulus if the time derivative of the contact force exceeds the threshold.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 3 is a schematic perspective illustration of a first embodiment of a sphincter contraction sensor.

FIG. 4 is a schematic cross-sectional view of the sphincter contraction sensor of FIG. 3, taken along line 4-4.

FIG. 5 is a schematic side-view illustration of a second embodiment of a sphincter contraction sensor.

FIG. 6 is a schematic cross-sectional view of the sphincter contraction sensor of FIG. 5, taken along line 6-6.

DETAILED DESCRIPTION

Figure 1:
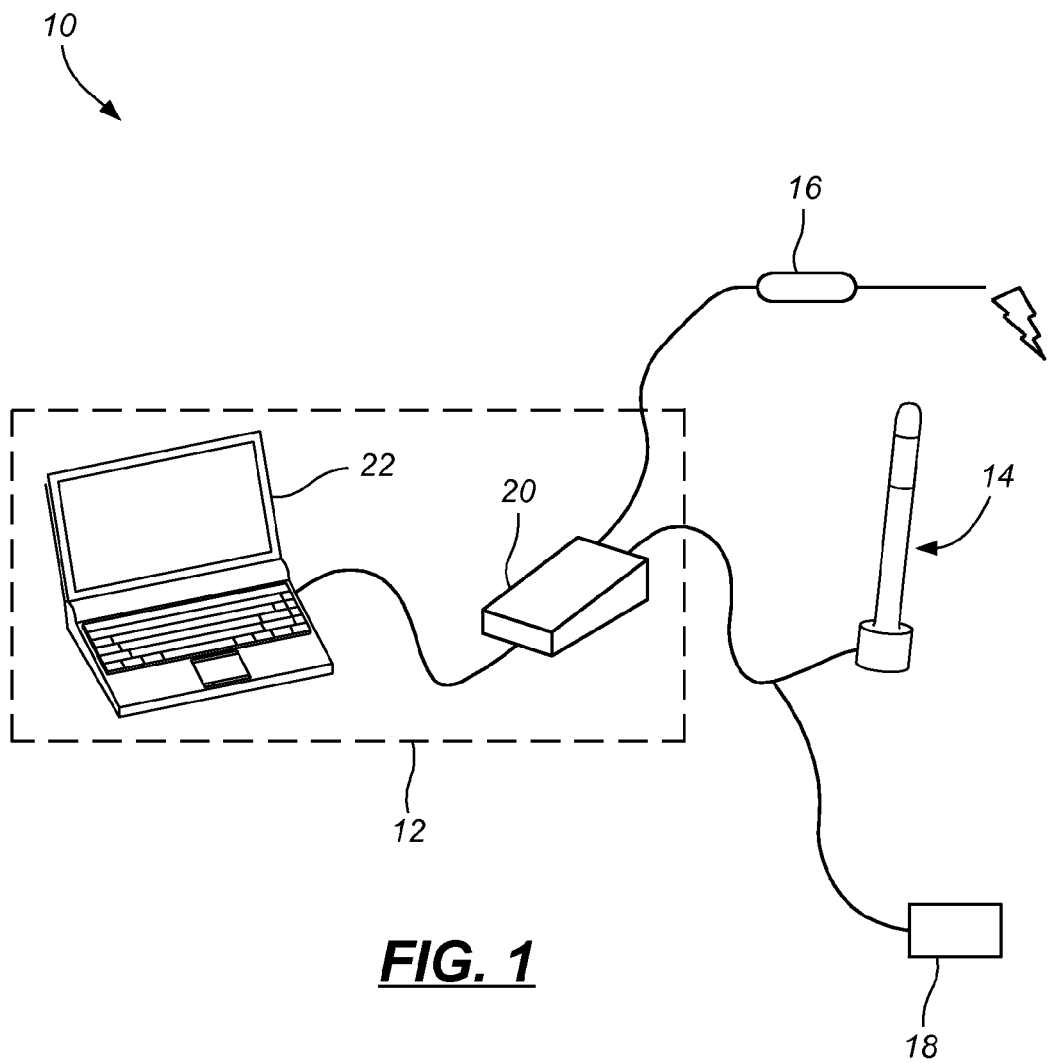
FIG. 1 is a schematic illustration of a mechanomyographic neural monitoring system.

Referring to the drawings, wherein like reference numerals are used to identify like or identical components in the various views, FIG. 1 schematically illustrates a neural monitoring system 10 configured to detect the presence of one or more sacral nerves within a human subject. As used herein, reference to "sacral nerves" includes, but is not limited to the pudendal nerve, the pelvic splanchnic nerve, the inferior hypogastric nerve, the inferior rectal nerve, the pelvic plexus, and/or any other nerve incorporated into the urinary, fecal, and/or sexual functioning of humans. The neural monitoring system 10 may include a receiver 12 in communication with a sphincter contraction sensor 14, a stimulator 16, and a ground patch 18. The receiver 12 may include, for example, a sensor interface 20 and a computing device 22. The computing device 22 may, in turn, include a processor, memory, and a display, and may be embodied as, for example, a personal computer, tablet computer, personal digital assistant (PDA), or the like. The sensor interface 20 may be configured to receive and present information from the sphincter contraction sensor 14 to the computing device 22, and may include, for example, communications circuitry, signal processing circuitry, and/or other associated interfacing circuitry. While shown as distinct components in FIG. 1, in an embodiment, the sensor interface 20 may be an integral part of the computing device 22.

Figure 2:
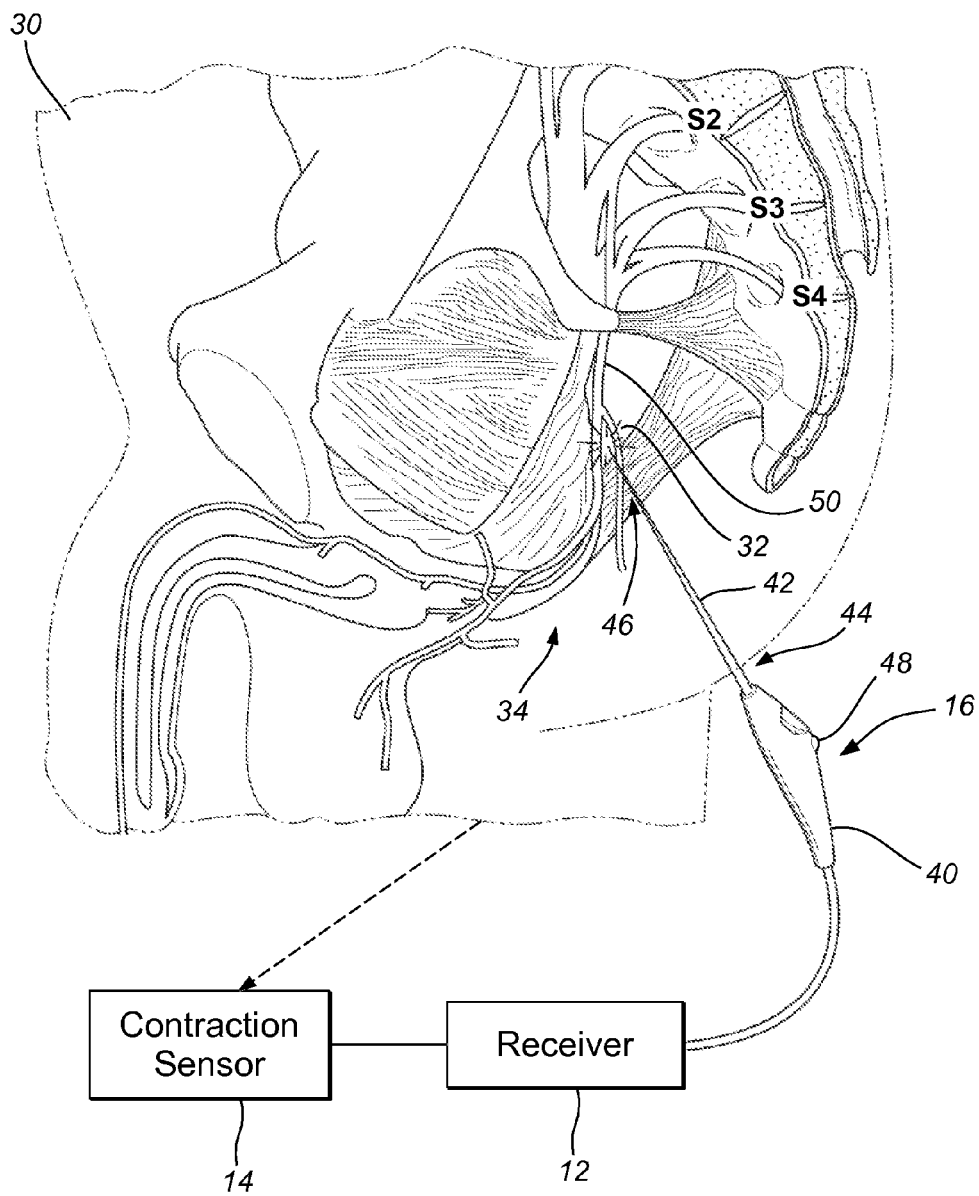
FIG. 2 is a schematic illustration of a mechanomyographic neural monitoring system used in conjunction with a human subject, where a stimulator is being used to provide an electrical stimulus proximate to a pudendal nerve of the subject.

FIG. 2 schematically illustrates an embodiment of the neural monitoring system 10 being used together with a human subject 30 to identify/detect the presence of one or more sacral nerves, such as the pudendal nerve. As shown, the stimulator 16 may be configured to provide an electrical stimulus 32 within an intracorporeal treatment area 34 of the subject 30. As used herein, the "intracorporeal treatment area" specifically refers to a surgical treatment area within the body of the subject 30 (i.e., sub-dermis). In particular, the presently described apparatus may be useful during surgical procedures in the lower abdomen. Such procedures may include surgical procedures on the bladder, prostate, colon, pelvis, or other neighboring organs.

The stimulator 16 may include a handle 40 coupled with a stimulator probe 42. The stimulator probe 42 may include a proximal end portion 44 and a distal end portion 46, with one or more electrodes disposed at or about the distal end portion 46. The stimulator 16 may be configured to selectively provide an electrical stimulus 32 from the one or more electrodes, wherein the electrical stimulus 32 may be transmitted to the subject 30 through direct contact between the one or more electrodes and the intracorporeal tissue (and/or fluid surrounding the tissue). In one configuration, the stimulator 16 may be configured to receive a request from a user/surgeon, and may energize the one or more electrodes to transmit the electrical stimulus 32 only in response to the received request. For example, the handle 40 of the stimulator 16 may include a button 48 the user may depress when an electrical stimulus 32 is desired. In other configurations, the stimulator 16 may transmit the stimulus in a continuous mode, where no request is required.

While one embodiment of a stimulator 16 may resemble a dissection probe, as generally illustrated in FIG. 2, other embodiments may generally resemble other elongate surgical instruments typically used in surgery. For example, the stimulator may include a scalpel, forceps, cautery probe, dilator, and/or retractor.

In one configuration, the stimulator 16 may be freely movable throughout the intracorporeal treatment area during a surgical procedure. In this manner, following an initial incision, a surgeon may use the stimulator probe 42 to test/sweep the surgical treatment area 34 to detect the presence of one or more nerves within the area 34. As such, the surgeon may use the neural monitoring system 10 to avoid damaging any nerves that may lie within the treatment area 34 during the procedure (as will be described in greater detail below).

FIG. 2 generally illustrates one surgical approach that may benefit from the present neural monitoring system 10. In particular, FIG. 2 illustrates a partial cross-sectional view of a human subject 30 with the stimulator probe 42 being used to provide a stimulus 32 to the subject through the pelvic floor. As shown, the pudendal nerve 50 is one of the sacral nerves that is expected to lie within the pelvic floor area of the human anatomy. The pudendal nerve 50 generally includes nerve fibers exiting the second, third, and fourth sacral vertebrae S2, S3, S4, and further includes various branches that subsequently split off to innervate the external sphincter of the anus and external sphincter of the bladder, among other things.

If the electrical stimulus 32 is provided at, or sufficiently close to the pudendal nerve 50, or any other sacral nerve within the treatment region 34, the stimulus 32 may be received by the nerve 50 in a manner that causes the nerve to depolarize. A depolarizing nerve may then induce a response in a muscle that is innervated by the nerve 50. One form of an evoked muscle response may manifest itself as a contraction of one or both of the external sphincter of the anus and external sphincter of the bladder. Likewise, another evoked muscle response may manifest itself as a contraction of one or both of the internal sphincter of the anus and external sphincter of the bladder. As will be discussed below, by placing a suitable force sensor within the sphincter, the receiver 12 may be capable of correlating a physical sphincter response (contraction), with an electrical stimulus 32 provided to the treatment area 34.

FIGS. 3 and 5 illustrate two potential embodiments of a sphincter contraction sensor 114, 214 (respectively). As shown, the sphincter contraction sensor 114 provided in FIG. 3 may be particularly suited for monitoring a contraction of the external sphincter of the bladder, while the sphincter contraction sensor 214 provided in FIG. 4 may be particularly suited for monitoring a contraction of the external sphincter of the anus (i.e., a "bladder sphincter contraction sensor 114" and an "anal sphincter contraction sensor 214", respectively). Each sphincter contraction sensor 114, 214 may be of a size and/or dimension to be inserted within an orifice defined by the respective sphincter. Likewise, each sphincter contraction sensor 114, 214 may be particularly configured to measure a physical response of the sphincter. The physical response may include a physical/mechanical contraction or relaxation of the sphincter; though, as used herein, a physical response should be viewed as distinct from an electrical and/or biochemical response (even if the various response-types may be inter-related under certain circumstances).

Referring to FIG. 3, one configuration of a bladder sphincter contraction sensor 114 may include an elongate device body 60 disposed along a longitudinal axis 62. The elongate device body 60 may include a proximal end portion 64 and a distal end portion 66, with the distal end portion being configured for insertion into the human subject 30. In one configuration, the elongate device body 60 may be a Foley Catheter. As used in the art, a Foley Catheter is a flexible tube 68 that may be passed through the urethra of a subject and into the bladder.

The flexible tube 68 may internally define two separated channels, or lumens that extend the length of the tube 68 along the longitudinal axis 62. A first lumen 70 may be open at both ends, and may be configured to allow urine to freely pass from the bladder into a collection bag. The second lumen 72 may be in fluid communication with an inflatable bulbous retention feature 74 (i.e., a balloon 76) disposed at the distal end portion 66 of the device body 60. Using the second lumen 72, the balloon 76 may be inflated with a sterile water and/or saline solution once inside the bladder to restrain the device body 60 from withdrawing from the bladder through the sphincter. The second lumen 72 may include a valve 78 at the proximal end portion 64 of the device body 60, which may restrict the flow of the sterile water out of the balloon 76.

The bladder sphincter contraction sensor 114 may further include a force sensor 90 in mechanical communication with the elongate device body 60 at a position along the longitudinal axis 62 where it may monitor a contraction of a sphincter against the device body 60. In one configuration, the force sensor 90 may be disposed at or near the distal end portion 66 of the elongate device body 60, though may be proximally located relative to the bulbous retention feature 74.

When in place within the sphincter of the subject, the force sensor 90 may be configured to generate a mechanomyography output signal 92 in response to a contact force applied against the elongate device body 60 by the tissue of the sphincter. For example, in one configuration, the force sensor 90 may include a pressure sensitive film 94 that may be circumferentially disposed about a portion of the device body 60. In other configurations, the force sensor 90 may include one or more strain gauges, piezoresistive strain gauges, capacitive force sensors, piezoelectric strain gauges, pneumatic pressure transducers, optical force transducers (e.g., fiber Bragg grating sensors), or any other known or hereinafter developed force sensors that may generate an output signal 92 in response to a contact force applied against the elongate device body 60. Likewise, the force sensor 90 may be disposed about the device body 60 in any orientation such that it can monitor a contact force applied against the elongate device body 60. For example, in one configuration the force sensor 90 may be circumferentially disposed about the device body 60, as mentioned above; in another configuration, however, the force sensor 90 may radially extend within the device body 60.

The mechanomyography output signal 92 may include one or more of a variable voltage signal, a variable current signal, a variable resistance, an analog pressure map, and/or a digital pressure map. Regardless of the form of the signal, the mechanomyography output signal 92 may correspond to either a magnitude or a change in magnitude of a contact force applied against the elongate device body 60 by the tissue of the sphincter.

FIG. 4 illustrates a schematic cross-sectional view of the bladder sphincter contraction sensor 114 shown in FIG. 3, taken along line 4-4. In this configuration, the contraction sensor 114 includes a generally circular device body 60 that defines a first lumen 70 and a second lumen 72. In this configuration, a pressure sensitive film 94 is circumferentially disposed about the device body 60, however, in other configurations, one or more discrete force sensors 90 may be disposed at various locations around the circumference of the device body 60. Finally, the bladder sphincter contraction sensor 114, may include a bio-compatible laminate 96 circumferentially disposed about the pressure sensitive film 94. Such a laminate 96 may be sufficiently thin to avoid altering the pressure-transducing functions or sensitivity of the film 94, however, it may act as a fluid barrier to allow proper functioning of the film 94.

FIG. 5 illustrates one configuration of an anal sphincter contraction sensor 214. Similar to the bladder sphincter contraction sensor 114, the anal sphincter contraction sensor 214 may include an elongate device body 120 disposed along a longitudinal axis 122. The elongate device body 120 may include a proximal end portion 124 and a distal end portion 126, wherein the distal end portion is configured for insertion into the human subject 30. As may be appreciated, the elongate device body 120 of the anal sphincter contraction sensor 214 may be particularly suited for insertion into the anus and/or rectal cavity of the subject 30, and may comprise an intra-anal plug.

As shown, the elongate device body 120 may include a bulbous retention feature 128 at the distal end portion 126, and may include a flared feature 130 at the proximal end portion 124. Furthermore, a necked portion 132 may be disposed between the proximal end portion 124 and the distal end portion 126. The necked portion 132 may have a narrower diameter than both the bulbous retention feature 128 and the flared feature 130. In this manner, upon insertion into the orifice defined by the anal sphincter, the anal sphincter may locate about the necked portion 132, where the bulbous retention feature 128 may restrain the device body 120 from being expelled from the subject, and the flared feature 130 may restrain the device body 120 from fully passing into the subject.

The anal sphincter contraction sensor 214 may further include a force sensor 140 in mechanical communication with the elongate device body 120 at a position along the longitudinal axis 122 where it may monitor a contraction of the anal sphincter against the device body 120. In one configuration, the force sensor 140 may be disposed at or near the necked portion 132 of the elongate device body 120, (i.e., proximal to the bulbous retention feature 128, and distal to the flared feature 130).

When in place within the sphincter of the subject, the force sensor 140 may be configured to generate a mechanomyography output signal 142 in response to a contact force applied against the elongate device body 120 by the tissue of the sphincter. For example, in one configuration, the force sensor 140 may include a pressure sensitive film 144 that may be circumferentially disposed about the necked portion 132 of the device body 120. In other configurations, the force sensor 140 may include one or more strain gauges, pneumatic pressure transducers, optical force transducers, or any other known or hereinafter developed force sensors that may generate an output signal 142 in response to a contact force applied against the elongate device body 120. The mechanomyography output signal 142 may be similar in nature to the mechanomyography output signal 92 described above, and may include one or more of a variable voltage signal, a variable current signal, a variable resistance, an analog pressure map, and/or a digital pressure map. Regardless of the form of the signal, the mechanomyography output signal 142 may correspond to either a magnitude or a change in magnitude of a contact force applied against the elongate device body 120 by the tissue of the sphincter.

FIG. 6 illustrates a schematic cross-sectional view of the anal sphincter contraction sensor 214 shown in FIG. 5, taken along line 6-6. In this configuration, the contraction sensor 214 includes a generally circular device body 120, and a pressure sensitive film 144 circumferentially disposed about the device body 120. In other configurations, instead of the film 144, one or more discrete force sensors 140 may be disposed around the circumference of the device body 120. Finally, the anal sphincter contraction sensor 214, may include a bio-compatible laminate 146 circumferentially disposed about the pressure sensitive film 144. Such a laminate 146 may be sufficiently thin to avoid altering the pressure-transducing functions or sensitivity of the film 144, however, it may act as a fluid barrier to allow proper functioning of the film 144.

Figure 7:
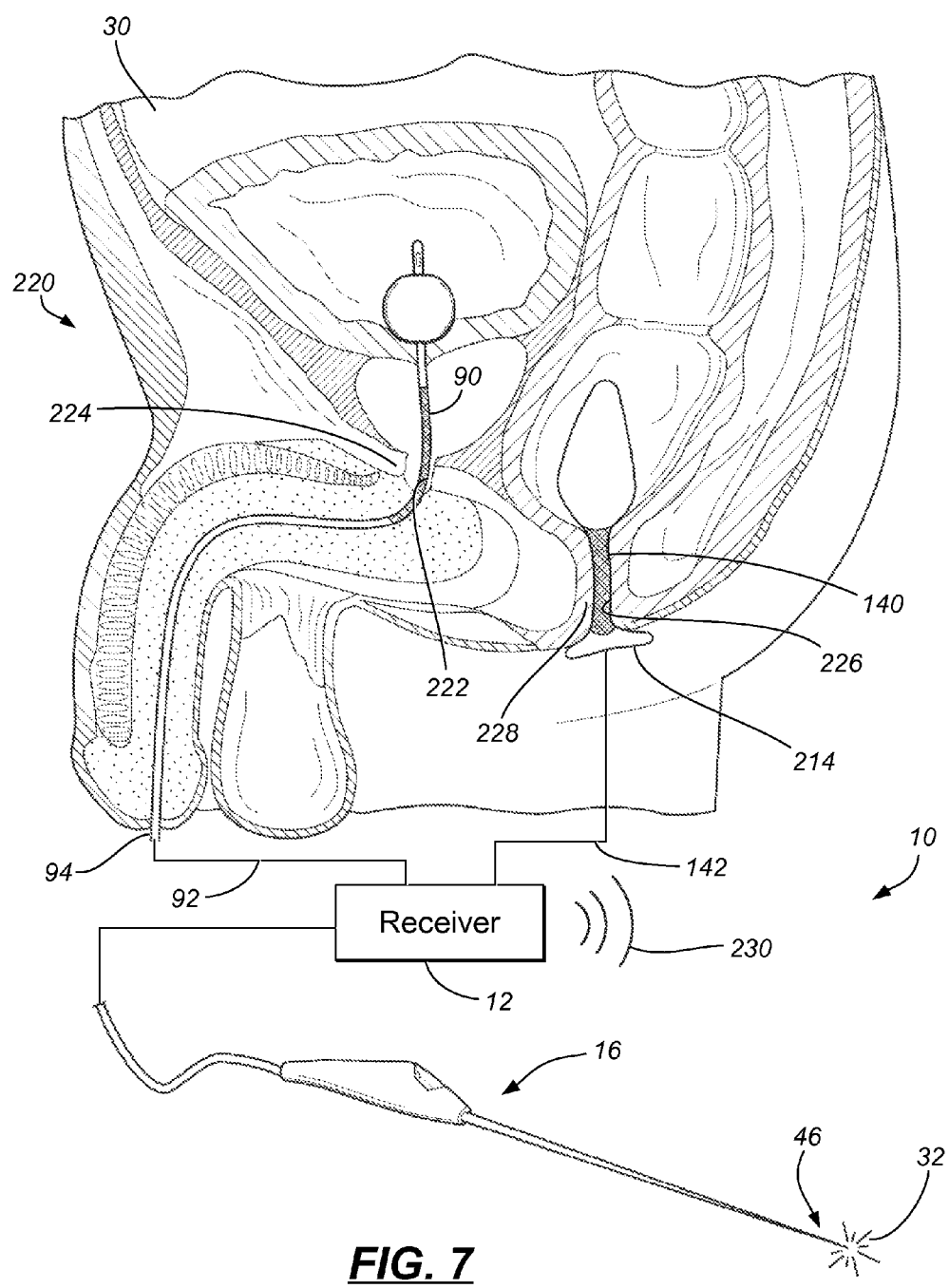
FIG. 7 is a schematic partial cross-sectional view of the first and second embodiments of a sphincter contraction sensor being used with a human subject.

FIG. 7 schematically illustrates a cross-sectional view of a portion 220 of a human subject 30, where both the bladder sphincter contraction sensor 114 and anal sphincter contraction sensor 214 are in an operational position within the subject 30. As shown, the bladder sphincter contraction sensor 114 is disposed within an orifice 222 defined by the external sphincter of the bladder 224, and the anal sphincter contraction sensor 214 is disposed within an orifice 226 defined by the external sphincter of the anus 228. Each sphincter contraction sensor 114, 214 includes a respective force sensor 90, 140 configured to be in positioned direct physical contact within the respective sphincter 224, 228. As described above, the respective force sensors 90, 140 may each generate a mechanomyography output signal 92, 142 in response to any sensed contact force by the sphincter against the device 114, 214.

Depending on the particular nature of the procedure, the neural monitoring system 10 may be fully operational using either of the two sphincter contraction sensors 114, 214, individually. Alternatively, a surgeon may choose to implement the system 10 using both contraction sensors 114, 214 together.

When both sphincter contraction sensors 114, 214 are used, each contraction sensor 114, 214 may be in respective electrical communication with the receiver 12. In this manner, the receiver 12 may be configured to receive the mechanomyography output signal 92 from the bladder sphincter contraction sensor 114 and the mechanomyography output signal 142 from the anal sphincter contraction sensor 214. The receiver 12 may then provide an indicator 230 to the surgeon based on at least a portion of the output signals 92, 142 received from one or both sphincter contraction sensors 114, 214. The indicator 230 may include a visual indicator and/or an audible indicator, and may convey to the surgeon that a physical sphincter contraction was detected. Additionally, the indicator 230 may indicate that a detected sphincter contraction was an involuntary sphincter contraction, and/or the indicator 230 may convey a determined proximity between the distal end portion 46 of the stimulator probe 16 and the one or more sacral nerves within the treatment region. As may be appreciated, a visual indicator may include a display image on a display device associated with the receiver. Such an image may include, for example, a "stop" indication, a "go/no-go" indication, a graph of sensor output, and/or a numeric representation of proximity.

Figure 8:
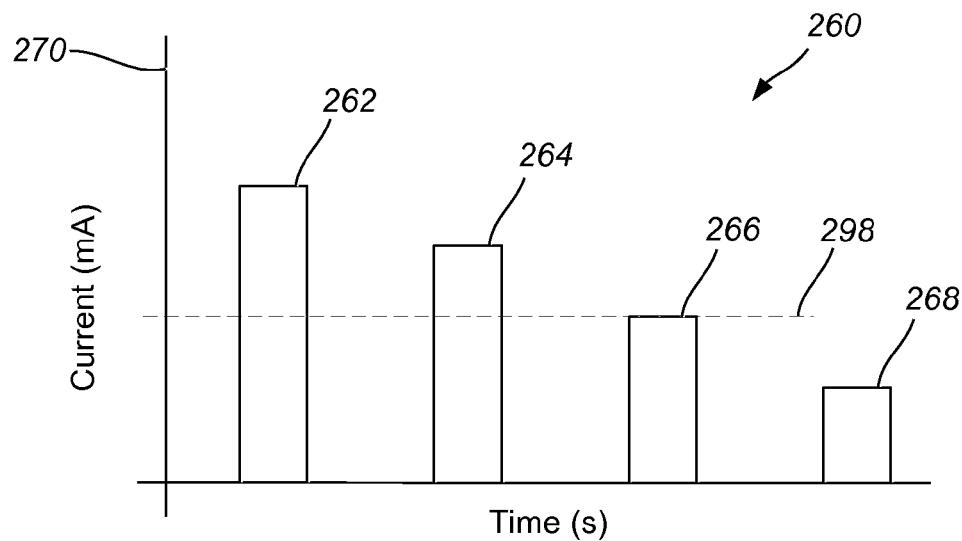
FIG. 8 is a schematic graph of a plurality of electrical stimulus pulses that may be provided to an intracorporeal treatment area of a subject, with stimulus current shown as a function of time.

During the neural testing/detection process, the receiver 12 may be in communication with both the stimulator 16 and one or both sphincter contraction sensors 114, 214. As such, the receiver 12 may receive an indication from the stimulator 16 when an electrical stimulus 32 is transmitted to the tissue and/or nerves residing within the tissue. FIG. 8 generally illustrates a current plot 260 of an electrical stimulus 32 provided to the subject 30. As shown, the electrical stimulus 32 may include a plurality of sequentially administered pulses 262, 264, 266, 268 (e.g., at a 0.5-2.0 Hz frequency). Depending on the application, each pulse may be provided at a different electrical current magnitude 270. Also, while FIG. 8 illustrates direct current (DC) stimulus pulses, the pulses may alternatively be alternating current (AC) pulses, each potentially being provided at a varying root-mean-squared (RMS) current.

Figure 9:
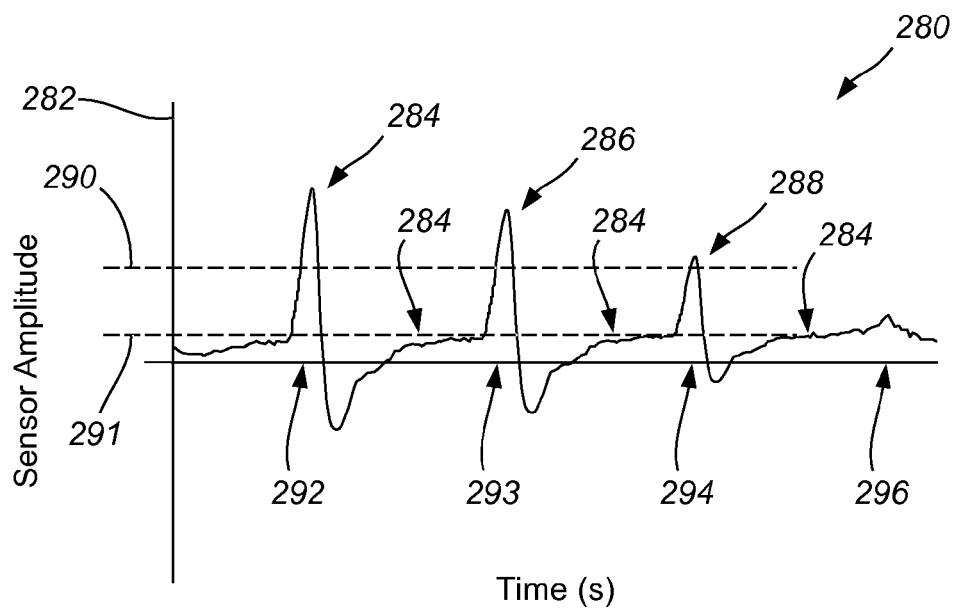
FIG. 9 is a schematic graph of a plurality of sphincter contraction responses that may be sensed in response to the transmission of the plurality of electrical stimulus pulses provided in FIG. 8.

FIG. 9 then illustrates a graph 280 of a sphincter contraction force amplitude 282 vs. time, that may be representative of a contact force applied by the sphincter tissue against the sphincter contraction sensors 114, 214, and which may be conveyed to the receiver via one of the mechanomyography output signals 92 and/or 142. The sphincter contraction force 282 illustrated in FIG. 9 may be representative of a sphincter response following the delivery of an electrical stimulus 32 of the type provided in FIG. 8. The sensed sphincter contraction force amplitude 282 may correspond to a plurality of detected sphincter contractions 284, 286, 288 and a plurality of relaxed states 289. As may be appreciated, the "relaxed" states 289 may be representative of a baseline contact force 291 that exists due to the automatic contraction of the sphincter. From this baseline 291, any somatic change in contraction force may cause the sphincter to either contract or relax, depending on the nerve involved (for simplicity, any somatic change in sphincter contraction (i.e., a somatic contraction or a somatic relaxation) will be generally referred to as a sphincter contraction).

In one configuration, a sphincter contraction may be detected by comparing the sensed sphincter contraction force 282 to a threshold 290. The threshold 290 may be dynamically set relative to a baseline (relaxed) contact force 291. As such, the receiver 12 may first examine the mechanomyography output signal 92, 194 to determine if a sphincter contraction/relaxation event has occurred. To accomplish this, the receiver 12 may compare any change in the sensed sphincter contraction force 282 to the baseline (automatic) contact force 291, which may be continuously updated. If the magnitude of the change exceeds a threshold amount of change, than the receiver 12 may indicate that a somatic contraction/relaxation has occurred. While shown in FIG. 9 as a positive threshold 290 relative to the baseline 291, it should also be understood that an induced response may involve a relaxation of the sphincter. As such, a similar negative threshold (not shown) may also be applied below the baseline to monitor for an induced relaxation.

The receiver 12 may use internal control logic to determine that a detected sphincter contraction was induced and/or was involuntary (such as generally at 292, 293, 294). In one configuration, this determination may be made by coordinating the sensed response with administered pulses 262, 264, 266 in time. As further shown, the sensor response generally at 296, following pulse 268 may neither register as a sphincter contraction, nor may have a steep enough response to be viewed as "induced." Such a result may be attributable to the current magnitude 270 of the pulse 268 being below a threshold current level 298 that would cause the nerve 50 to begin depolarizing given the distance between the stimulator 16 and the nerve 50.

Figure 10:
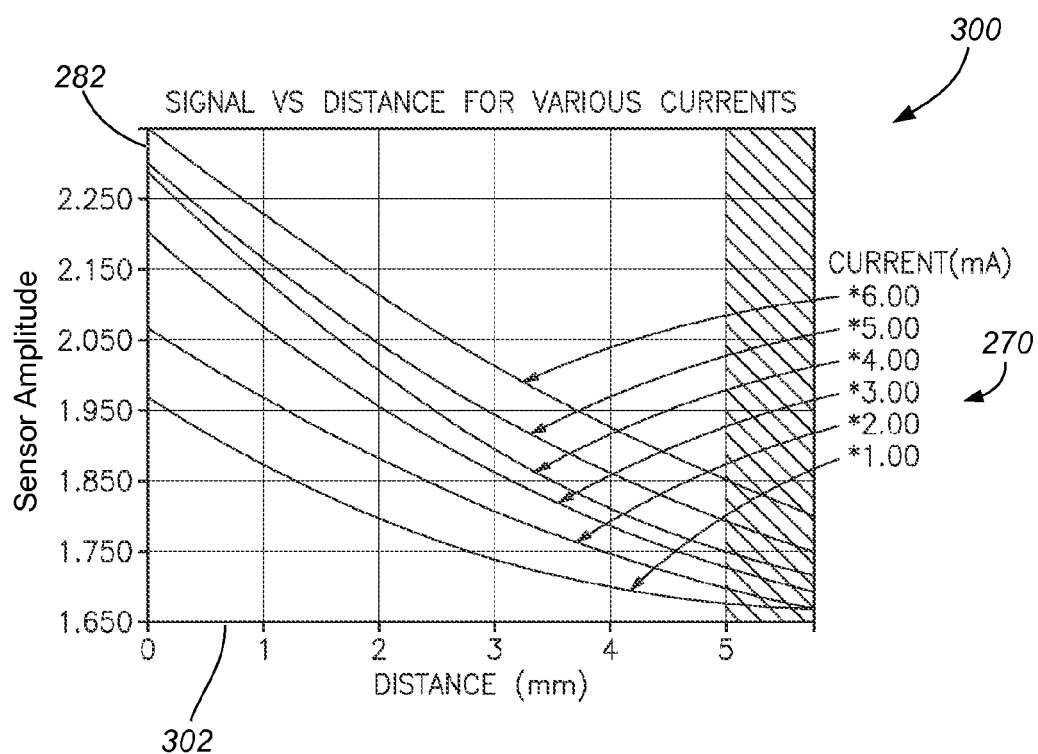
FIG. 10 is a schematic graphic representation of a look-up table that may be used to determine nerve proximity from the distal end portion of a stimulator probe, given a known electrical stimulus amplitude, and a sensed sphincter contraction amplitude.

FIGS. 8 and 9 further illustrate the correlation between the provided current 270 of the electrical stimulus 32, and the amplitude 282 of the monitored sphincter contraction/contact force, given a fixed distance between the distal end portion 46 of the stimulator probe 42 and the nerve 50. FIG. 10 graphically illustrates an example (i.e., a graph 300) of the interrelation of monitored contact force amplitudes 282, electrical stimulus current levels 270, and distances 302 between the distal end portion 46 of the stimulator probe 42 and the nerve 50. The receiver 12 may maintain this interrelation (e.g., graph 300) as a lookup table within memory associated with the receiver 12. In this manner, the receiver 12 may determine the proximity (i.e., distance 302) between the distal end portion 46 of the stimulator probe 42 and the nerve 50, by selecting the distance 302 from table 300, given its knowledge of the current magnitude 270 and sensed contact force amplitude 282.

As generally mentioned above, the receiver 12 may include various means to determine if a sensed sphincter contraction (as conveyed by the mechanomyography output signal 92) corresponds to, or was induced by a an electrical stimulus 32 provided by the stimulator 16. While coordination in time may be one way of accomplishing such a correlation, it may be similarly possible to identify an induced/involuntary contraction by examining one or more response properties of the mechanomyography output signal 92. For example, the speed of the response/contraction may be one parameter that may suggest an induced response. Likewise, an acceleration of the response and/or a time derivative of the acceleration may be monitored to suggest an induced/involuntary response. In each of the three derivatives of contact force (speed, accel., and da/dt), an induced response generally has a greater magnitude than a patient-intended response. In this manner, the receiver 12 may be configured to compute one or more time derivatives of the monitored contact force from the received mechanomyography output signal 92. The receiver 12 may then compare the computed time derivative of the contact force to a threshold, and determine that mechanomyography output signal 92 corresponds to the electrical stimulus 32 provided by the stimulator 16 if the time derivative of the contact force exceeds the threshold.

Figure 11:
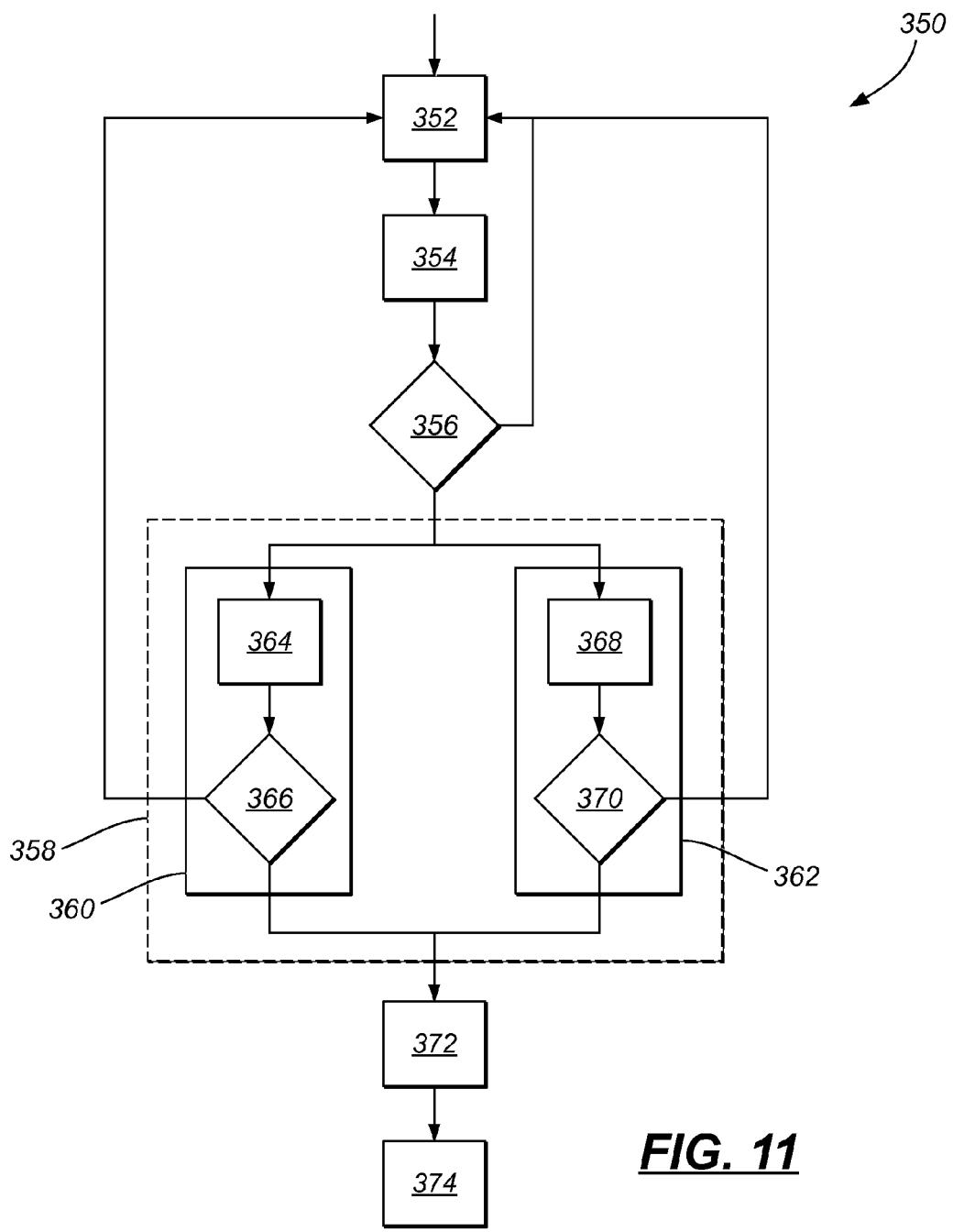
FIG. 11 is a schematic flow diagram of a method of detecting an induced sphincter contraction using a neural monitoring system.

FIG. 11 illustrates one embodiment of a method 350 of detecting an inducted sphincter contraction using a neural monitoring system 10 of the kind described above. The method 350 begins by physically monitoring a contraction of at least one of the external sphincter of the bladder and the external sphincter of the anus using a force sensor disposed within an orifice defined by the respective sphincter (at 352). Step 352 may be performed by an elongate sphincter contraction sensor that includes an elongate device body and a force sensor in mechanical communication with the elongate device body. The contraction monitoring accomplished in step 352 may include generating a mechanomyography output signal in response to a contact force of the sphincter against the force sensor and/or device body.

A receiver may then continuously monitor the mechanomyography output signal in step 354 to detect a sphincter contraction. The receiver may determine the existence of the sphincter contraction, for example, by calculating a change in magnitude of the mechanomyography output signal over a discrete period of time. If the change in magnitude exceeds a particular threshold (at 356), the receiver may then attempt to determine if the detected sphincter contraction was induced by a surgeon-provided stimulus (at 358). If the change in magnitude does not exceed the threshold, the sensor/receiver may continue monitoring the sphincter response.

As described above, the receiver may be configured to determine that a detected sphincter contraction was induced by a surgeon-provided stimulus by either coordinating the response in time with a provided stimulus (at 360), or by further examining properties of the mechanomyography output signal (at 362). In some configurations, the system may use both time coordination 360 and signal properties 362 to detect an induced response.

To coordinate the response in time with a provided stimulus 360, the receiver may first receive an indication that a stimulus was administered to a treatment area of the subject (at 364). It may subsequently calculate the difference in time between when the stimulus was administered and when the response was detected (i.e., when the change in magnitude exceeded the threshold). If the calculated time is below a threshold amount of time (at 366), then the receiver may conclude that the detected response was induced by the electrical stimulus, otherwise, it may reject the response as not being temporally relevant.

Further examining properties of the mechanomyography output signal to detect an induced response (at 362) may include computing one or more time derivatives of the mechanomyography output signal (at 368), and comparing the computed time derivative(s) to a threshold (at 370). If a computed time derivative exceeds the threshold, then the receiver may conclude that the detected response was an involuntary and/or was an induced response to the electrical stimulus, otherwise, it may reject the response as not being of the kind/nature that is expected to occur in response to an administered stimulus and/or an induced depolarization of the nerve.

Once an induced response is detected/determined, the receiver may estimate a distance between the distal end portion of the stimulator probe and the nerve using the magnitude of the current of the applied stimulus and the change in magnitude of the mechanomyography output signal (at 372). For example, the receiver may use the two known values (stimulus amplitude and contraction response) to select a distance from a two-dimensional lookup table.

The receiver may then provide an indicator to a user (at 374) that may indicate that an induced/involuntary sphincter contraction was detected and/or may indicate an estimated proximity between the distal end portion of the stimulator probe and the nerve.

While FIG. 11 illustrates one potential method 350 of detecting an induced sphincter contraction using a neural monitoring system 10, this method 350 should be illustrative, as other methods may likewise be available.

Furthermore, while the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A method of detecting the presence of a sacral nerve in a human subject, the method comprising:
  providing an electrical stimulus via a distal end portion of an elongate stimulator disposed within an intracorporeal treatment area of the human subject, wherein the electrical stimulus has a magnitude;
  detecting a magnitude of a physical response of at least one of an external sphincter of the subject's bladder and an external sphincter of the subject's anus using a mechanical sensor disposed on an elongate sphincter contraction sensor,
  determining, via a processor in communication with the elongate stimulator and the mechanical sensor, if the physical response was induced by the provided electrical stimulus;
  determining, via the processor, a distance between the distal end portion of the elongate stimulator and the sacral nerve using the magnitude of the provided electrical stimulus and the magnitude of the physical response; and
  comparing the determined distance to a threshold;
  providing a first indicator via a display if the physical response was induced by the provided electrical stimulus and the determined distance is less than the threshold; and
  providing a second indicator via the display if the physical response was induced by the provided electrical stimulus and the determined distance is greater than the threshold.

2. The method of claim 1, wherein the physical response includes a contact force between the at least one of the external sphincter of the subject's bladder and the external sphincter of the subject's anus and the mechanical sensor;
  the method further comprising:
  computing a time derivative of the magnitude of the contact force;
  comparing the time derivative of the contact force to a threshold; and
  determining that the physical response was induced by the provided electrical stimulus if the time derivative of the contact force exceeds the threshold; and
  displaying an indication via the display if it is determined that the physical response was induced by the provided electrical stimulus.

3. A method of detecting the presence of a sacral nerve in a human subject, the method comprising:
- providing an electrical stimulus from the distal end of an elongate stimulator disposed within an intracorporeal treatment area of the human subject;
- generating a mechanomyography output signal using a force sensor disposed within an orifice defined by at least one of an external sphincter of the subject's bladder and an external sphincter of the subject's anus, the mechanomyography output signal corresponding to a contact force of at least one external sphincter of the bladder and the external sphincter of the anus against the force sensor;
- detecting, via a processor in communication with the elongate stimulator and the force sensor, an involuntary contraction of at least one of the external sphincter of the bladder and the external sphincter of the anus using the mechanomyography output signal and an indication of the provided electrical stimulus;
- determining a distance, via the processor, between the distal end of the elongate stimulator and the sacral nerve from a magnitude of the mechanomyography output signal and a magnitude of the provided electrical stimulus;
- providing an indication to a user of the determined distance if an involuntary contraction is detected.

4. The method of claim 3, wherein providing an electrical stimulus includes selectively administering the electrical stimulus from the elongate stimulator.

5. The method of claim 3, wherein detecting an involuntary contraction includes:
- calculating a change in the magnitude of the contact force from the mechanomyography output signal;
- comparing the change in the magnitude of the contact force to a threshold; and
- detecting an involuntary sphincter contraction if the change in the magnitude of the contact force exceeds the threshold.

6. The method of claim 3, wherein detecting an involuntary contraction includes:
- computing a time derivative of the contact force from the mechanomyography output signal;
- comparing the time derivative of the contact force to a threshold; and
- detecting an involuntary contraction if the time derivative of the contact force exceeds the threshold.

7. The method of claim 3, further comprising providing an elongate sphincter contraction sensor configured to be inserted within at least one of an external sphincter of the bladder and an external sphincter of the anus;
- wherein the elongate sphincter contraction sensor includes an elongate device body having a proximal end portion and a distal end portion; and
- wherein the force sensor includes a pressure sensitive film circumferentially disposed about a portion of the elongate device body.

8. The method of claim 7, wherein the elongate device body further includes a bulbous retention feature distally disposed in relation to the force sensor, the bulbous retention feature configured to restrain passage of the elongate body through the sphincter.

9. The method of claim 3, wherein the involuntary contraction is a contraction caused by the depolarization of the sacral nerve in response to the provided electrical stimulus.

10. The method of claim 1, wherein determining the distance between the distal end portion of the elongate stimulator and the sacral nerve using the magnitude of the provided electrical stimulus and the magnitude of the physical response includes:
- selecting a distance value from a lookup table stored in a memory associated with the processor.

11. The method of claim 10, wherein the lookup table provides the distance as a function of both a variable electrical stimulus and a variable physical response magnitude.

12. The method of claim 1, wherein determining the distance between the distal end portion of the elongate stimulator and the sacral nerve using the magnitude of the provided electrical stimulus and the magnitude of the physical response includes:
- maintaining, in memory associated with the processor, a model of distance as a function of both a variable electrical stimulus and a variable magnitude of the physical response; and
- determining the distance using the model.

13. The method of claim 3, wherein determining the distance between the distal end portion of the elongate stimulator and the sacral nerve from a magnitude of the mechanomyography output signal and a magnitude of the provided electrical stimulus includes:
- selecting a distance value from a lookup table stored in a memory associated with the processor.

14. The method of claim 13, wherein the lookup table provides the distance as a function of both a variable electrical stimulus and a variable mechanomyography output signal magnitude.

15. The method of claim 3, wherein determining the distance between the distal end portion of the elongate stimulator and the sacral nerve from a magnitude of the mechanomyography output signal and a magnitude of the provided electrical stimulus includes:
- maintaining, in memory associated with the processor, a model of distance as a function of both a variable electrical stimulus and a variable magnitude of the mechanomyography output signal; and
- determining the distance using the model.

16. A method comprising:
- providing an electrical stimulus from a distal end portion of an elongate stimulator configured to extend within an intracorporeal treatment area of a subject;
- detecting a change in a magnitude of a contact force exerted against an elongate force sensor configured to extend within a natural orifice of the subject;
- determining, via a processor, if the change in the magnitude of the contact force was induced by the provided electrical stimulus;
- determining, via the processor, a distance between the distal end portion of the elongate stimulator and a nerve of the subject using a magnitude of the provided electrical stimulus and the magnitude of the contact force; and
- comparing the determined distance to a threshold;
- displaying a first indicator via a display if the detected change in the magnitude of the contact force was caused by the provided electrical stimulus and the determined distance is less than the threshold; and
- displaying a second indicator via the display if the detected change in the magnitude of the contact force was caused by the provided electrical stimulus and the determined distance is greater than the threshold.

17. The method of claim 16, wherein the second indicator is indicative that it is safe to proceed with a surgical procedure.

18. The method of claim 16, wherein the distance is determined by selecting a distance value from a look up table according to the magnitude of the provided electrical stimulus and the magnitude of the contact force.

19. The method of claim 18, wherein the lookup table provides the distance as a function of both a variable electrical stimulus and a variable contact force magnitude.

20. The method of claim 16, wherein determining the distance between the distal end portion of the elongate stimulator and a nerve of the subject using a magnitude of the provided electrical stimulus and the magnitude of the contact force includes:
   maintaining, in memory associated with the processor, a model of distance as a function of both a variable electrical stimulus and a variable magnitude of the physical response; and
   determining the distance using the model.

21. The method of claim 16, wherein the natural orifice of the subject includes at least one of an external sphincter of the subject's bladder and an external sphincter of the subject's anus.

* * * * *